United States Patent
Lin et al.

(10) Patent No.: US 6,790,959 B1
(45) Date of Patent: Sep. 14, 2004

(54) PROCESS FOR MANUFACTURING THEBAINE

(75) Inventors: Zhaiwei Lin, Plymouth, IN (US); Charles Auxilium Francis, Valparaiso, IN (US); Christopher Arne Kaldahl, LaPorte, IN (US); Kazimierz Grzegorz Antczak, Culver, IN (US); Vijai Kumar, Morris Plains, NJ (US)

(73) Assignee: Halsey Drug Company, Inc., Rockford, IL (US)

( * ) Notice: Subject to any disclaimer, the term of this patent is extended or adjusted under 35 U.S.C. 154(b) by 6 days.

(21) Appl. No.: 10/455,197

(22) Filed: Jun. 5, 2003

(51) Int. Cl.$^7$ .............................................. C07D 471/08
(52) U.S. Cl. ........................................................ 546/44
(58) Field of Search ............................................ 546/44

(56) References Cited

U.S. PATENT DOCUMENTS

| | | | |
|---|---|---|---|
| 3,894,026 A | 7/1975 | Sohar et al. | 260/285 |
| 4,045,440 A | 8/1977 | Rapoport et al. | 260/285 |
| 6,008,355 A | 12/1999 | Huang et al. | 546/45 |
| 6,067,749 A | 5/2000 | Fist et al. | 47/58.1 |
| 6,090,943 A | 7/2000 | Mudryk et al. | 546/44 |

OTHER PUBLICATIONS

Coop et al, "A Novel Synthesis of Thebaine, etc" Heterocycles, *49*, 1998, pp. 43–47.*

* cited by examiner

*Primary Examiner*—Patricia L. Morris
(74) *Attorney, Agent, or Firm*—Jack Matalon

(57) ABSTRACT

Thebaine is manufactured in high yields and with a high purity using codeine or a salt of codeine as the starting material. The manufacturing process involves the following steps:

(a) codeine or a codeine salt (e.g., codeine phosphate) is converted into the intermediate N-carboalkoxy- or N-carboaryloxynorcodeine;

(b) the intermediate N-carboalkoxy- or N-carboaryloxynorcodeine resulting from step (a) is oxidized to yield the intermediate N-carboalkoxy- or N-carboaryloxynorcodeine;

(c) the intermediate N-carboalkoxy- or N-carboaryloxynorcodeinone resulting from step (b) is enolized with a base and the resultant enolate is thereafter methylated to yield the intermediate N-carboalkoxy- or N-carboaryloxynorthebaine; and (d) the intermediate N-carboalkoxy- or N-carboaryloxynorthebaine resulting from step (c) is reduced to yield thebaine.

16 Claims, No Drawings

PROCESS FOR MANUFACTURING THEBAINE

FIELD OF THE INVENTION

Thebaine is manufactured in high yields and in a highly pure form by a multi-step manufacturing process that utilizes codeine or a codeine salt as the starting material.

BACKGROUND OF THE INVENTION

Thebaine is a minor component of opium. The supply of thebaine is limited, and the demand is increasing; therefore, the price of thebaine is high.

Thebaine is an important starting material for many useful compounds, particularly 14-hydroxy-substituted morphine derivatives that are important narcotic analgesics and/or antagonists, e.g., oxycodone, oxymorphone, nalbuphine, naloxone, naltrexone and nalmefene. A very useful narcotic, which is an oripavine derivative of thebaine, is buprenorphine, which is an ideal pharmacotherapy for the treatment of cocaine opiate abuse.

The starting material for the process of the present invention is codeine or a salt thereof. Codeine along with morphine, thebaine and oripavine may be extracted from poppy straw—see U.S. Pat. No. 6,067,749 issued May 30, 2000 to Fist et al. Codeine is also readily prepared by the methylation of morphine, which is present in poppy straw in a higher percentage than that of codeine.

Column 1, lines 37–45 of U.S. Pat. No. 6,008,355 describe several prior art methods for preparing thebaine: For example, codeine may be converted to thebaine through codeinone or through the 6-methyl ether of codeine.

Column 1, line 44 to column 2, line 56 of U.S. Pat. No. 6,090,943 also describe a number of prior art methods for the preparation of thebaine. The '943 patent itself discloses a process for preparing thebaine or thebaine analogs containing a dienol ester or a dienol ether, from morphinone, codeinone or analogs thereof which contain an $\alpha,\beta$-unsaturated ketone via an alkoxylated intermediate.

All of the prior art methods for preparing thebaine from codeine or a salt thereof are disadvantageous from a commercial manufacturing point of view in several respects. The purity of the thebaine is relatively low, thereby requiring considerable additional costly purification steps (and attendant loss of yield) to raise the purity to an acceptable level. A second disadvantage of the prior art methods is that they require the use of expensive reagents and the reactions are very time-consuming and are quite sensitive to reaction conditions. Thirdly, and most importantly, the prior art methods results in poor yields of thebaine and therefore such methods are unsuitable for commercial manufacturing operations.

OBJECTS OF THE INVENTION

It is the principal object of this invention to prepare thebaine with a high level of purity and sufficiently high yields so as to result in a commercially feasible manufacturing operation.

DETAILED DESCRIPTION OF THE INVENTION

The process of the invention for the manufacture of thebaine comprises the following steps:
(a) converting codeine or a codeine salt into the intermediate N-carboalkoxy- or N-carboaryloxynorcodeine;
(b) oxidizing the intermediate N-carboalkoxy- or N-carboaryloxynorcodeine to yield the intermediate N-carboalkoxy- or N-carboaryloxynorcodeine;
(c) enolizing the intermediate N-carboalkoxy- or N-carboaryloxynorcodeinone with a base and methylating the resultant enolate to yield the intermediate N-carboalkoxy- or N-carboaryloxynorthebaine; and
(d) reducing the intermediate N-carboalkoxy- or N-carboaryloxynorthebaine to yield thebaine.

Step (a) may be carried out by reacting the codeine or a codeine salt, e.g., codeine phosphate, with a chloroformate in the presence of an alkali metal carbonate or alkali metal bicarbonate and an inert solvent. Preferably, the chloroformate is a methyl, ethyl or phenylchloroformate. The alkali metal is typically sodium or potassium. Suitable examples of the inert solvent that may be used in step (a) include methylene chloride, chloroform, 1,2-dichloroethane and the like. Typically, the selected chloroformate will be utilized in an amount of about 1.5 to about 8.0 moles per mole of codeine or codeine salt. In general, the inert solvent will be present in the amount of about 10 to about 60, preferably 20 to 25, liters per kilogram of codeine or the selected codeine salt. The reaction involved in step (a) may be carried out at a temperature of about 0 to about 85° C., preferably 42–70° C., e.g., when the selected inert solvent is chloroform, the reaction is typically carried out under reflux at 65° C. The reaction time will typically be in the range of about 10 to about 72 hours, preferably 10 to 24 hours. The reaction in step (a) proceeds smoothly and completion of the reaction may be determined by high-pressure liquid chromatography.

Preferably, the intermediate N-carboalkoxy- or N-carboaryloxynorcodeine is not isolated, and step (b) is carried out in the same reaction vessel as employed for step (a).

Step (b) may be carried out by oxidizing the intermediate N-carboalkoxy- or N-carboaryloxynorcodeine with a suitable oxidizing agent in the presence of an inert solvent (which may be the same inert solvent as employed in step (a)). Suitable oxidizing agents include aluminum alkoxide and a ketone; a potassium alkoxide and a ketone; dimethyl sulfoxide in the presence of oxalyl chloride; manganese dioxide; potassium dichromate in the presence of sulfuric acid; and air in the presence of palladium (II) acetate. The preferred oxidizing agent comprises manganese dioxide. In general, the oxidizing agent will be used in an amount of about 7 to about 9 moles per mole of N-carboalkoxy- or N-carboaryloxynorcodeine.

Useful inert solvents for carrying out step (b) include chlorinated hydrocarbons such as chloroform, methylene chloride, 1,2-dichloroethane and the like; hydrocarbons such as benzene or toluene; esters such as ethyl acetate; and ethers such as tetrahydrofuran. The preferred solvents are chloroform and toluene. In general, the inert solvent will be utilized in an amount of about 10 to about 50, preferably 20 to 25, liters per kg of the intermediate resulting from step (a).

The oxidation reaction of step (b) may be carried out at temperatures of about 0 to about 60° C., preferably 20–25° C. Typically, the oxidation reaction for step (b) will entail a reaction time of about 6 to about 48, preferably 18 to 24, hours.

Preferably, the intermediate N-carboalkoxy- or N-carboaryloxynorcodeinone produced in step (b) is not isolated, and step (c) is carried out in the same reaction vessel as employed for step (b).

In step (c), the intermediate N-carboalkoxy- or N-carboaryloxynorcodeinone produced in step (b) is enolized using a base in an inert solvent and the resultant dienolate salt is thereafter methylated using a methylating agent. Suitable bases for carrying out the enolization reaction include sodium hydride, sodium t-butoxide, potassium t-butoxide and lithium diisopropylamide. Suitable inert solvents for carrying out the enolization reaction (and the subsequent methylation reaction) include tetrahydrofuran, N-methylpyrrolidinone, dimethylformamide, toluene, dimethyl ether, methyl t-butyl ether, dioxane and the like. The preferred solvent for carrying out both the enolization and the methylation reactions in step (c) comprises a mixture of about 1 part to about 20, preferably 4 parts, of tetrahydrofuran per part of N-methylpyrrolidinone. In general, the inert solvent employed in step (c) is employed in an amount of about 10 to about 50, preferably 20 to 30, liters per kg of the intermediate N-carboalkoxy- or N-carboaryloxynorcodeinone produced in step (b).

The methylation reaction may be carried out with typical methylating agents such as dimethyl sulfate, dimethyl carbonate, methyl iodide, methyl bromide, diazomethane and the like. In general, the methylating agent will be employed in an amount of about 2 to about 4 moles per mole of N-carboalkoxy- or N-carboaryloxynorcodeinone.

The enolization reaction as well as the subsequent methylation reaction involved in step (c) are typically conducted at temperatures in the range of about −20 to about 50° C., preferably −5 to 5° C. The typical reaction time for carrying out both the enolization reaction as well as the methylation reaction involved in step (c) will be about 2 to about 24, preferably 8 to 15, hours.

Preferably, the intermediate N-carboalkoxy- or N-carboaryloxynorthebaine produced in step (c) is not isolated, and step (d) is carried out in the same reaction vessel as employed for step (c).

In step (d), the intermediate N-carboalkoxy- or N-carboaryloxynorthebaine is reduced to yield the intermediate thebaine. The reducing agent preferably comprises lithium aluminum hydride or sodium bis(2-methoxyethoxy) aluminum hydride (boranetetrahydrofuran complex or borane-dimethyl sulfide complex may also be used). The reaction is generally carried out in an inert solvent such as tetrahydrofuran (which is preferred), dimethyl ether, diethyl ether, methyl t-butyl ether, and the like. Typically, such inert solvent will be utilized in an amount of 10 to about 50, preferably 20 to 30, liters per kg of the intermediate N-carboalkoxy- or N-carboaryloxynorthebaine produced in step (c).

In general, the reducing agent will be employed in step (d) in an amount of about 1 to about 3 moles per mole of N-carboalkoxy- or N-carboaryloxynorthebaine. In general, step (d) is carried out a temperature of about to about 60° C., preferably 20 to 25° C. The typical reaction time for carrying out the reduction reaction involved in step (d) will be about 1 to about 20, preferably 8–12, hours.

Preferably, the intermediate thebaine produced in step (d) is isolated as an acid addition salt. The isolation of the thebaine as an acid addition salt preferably involves the reaction of the thebaine with L-tartaric acid in a $C_1$–$C_4$ alcohol, acetone or a mixture thereof with water. In general, the isolation of the thebaine entails the use of about 1 to about 1.5 moles of L-tartaric acid per mole of thebaine produced in step (d). Typically, the $C_1$–$C_4$ alcohol, acetone or a mixture thereof with water will be utilized in an amount of about 5 to about 20, preferably 10–15, parts of such solvent per part of thebaine produced in step (d). If a mixture of the $C_1$–$C_4$ alcohol or acetone with water is utilized as the solvent, the water may be present in an amount of about 5 parts to about 20 parts per 100 parts of the $C_1$–$C_4$ alcohol or acetone. The preferred solvent is a mixture of methanol and water. The isolated thebaine bitartrate addition salt is recovered in a very high yield with a very high level of purity as a result of this isolation technique.

The following nonlimiting examples shall serve to illustrate the preferred embodiments of the present invention. Unless otherwise indicated to the contrary, amounts and percentages are on a weight basis.

EXAMPLE 1

Preparation of N-Carboethoxynorcodeine

A 500 ml round-bottomed flask is charged with 20 g of codeine phosphate hemihydrate, 120 ml of chloroform, 60 ml of water and 17 ml of concentrated (28–30%) aqueous ammonia. The mixture is stirred for a minimum of 20 minutes, the stirring is stopped and the layers are allowed to separate. The bottom organic layer is separated, washed with 25 ml of water and diluted with an additional 170 ml of chloroform.

The chloroform solution is heated to reflux and dried azeotropically until no water separation is observed (3 to 5 hours). After cooling to room temperature, 8.5 g of fine anhydrous potassium carbonate is added and the reaction mixture is heated to reflux. With vigorous stirring while under reflux, a solution of 13.5 g of ethylchloroformate in 85 ml of chloroform is added to the reaction mixture over a period of 1 to 2 hours. Thereafter, the reaction mixture is stirred while under reflux until the reaction is complete, typically 6 to 12 hours.

With stirring, approximately 300 ml of solvent is distilled off under reduced pressure (e.g., 50 mm Hg). Thereafter, 330 ml of toluene is added, with stirring, to the reaction mixture and the distillation is continued until all of the chloroform has been replaced by the toluene. The reaction mixture is cooled to room temperature. The inorganic salts are filtered off and the filter cake is washed with 30 to 50 ml of toluene. The volume of the filtrate is then adjusted to a total of 305 ml with additional anhydrous toluene. The filtrate contains 16.4 g (93% yield) of the intermediate N-carboethoxynorcodeine having a purity of greater than 95% as measured by HPLC. The intermediate is an oil and the toluene solution is used in step (b) (i.e., Example 2) without purification.

EXAMPLE 2

Preparation of N-Carboethoxynorcodeine

Manganese dioxide is added at the rate of about 8 g/hour, with vigorous stirring, to the toluene solution of the N-carboethoxynorcodeine obtained in Example 1. Typically, a total of 32–34 g of manganese dioxide is required to complete the oxidation reaction involved in step (b) of the process of the invention. The reaction time for the oxidation reaction is typically 6 to 12 hours. The manganese dioxide is filtered off and the filter cake is washed with three 40 ml portions of toluene. The filtrates are combined and the toluene solution is distilled under reduced pressure (e.g., 50 mm Hg) until the final volume has reached 34 ml. Thereafter, 180 ml of tetrahydrofuran is added to the residue. The tetrahydrofuran solution contains 15.5 g (95% yield) of N-carboethoxynorcodeinone having a typical purity of greater than 93% as measured by HPLC. The product is an oil and is used in step (c) (i.e., Example 3) without purification.

EXAMPLE 3

Preparation of N-Carboethoxynorthebaine

Into a 500 ml round-bottomed flask is charged 14.7 g of potassium t-butoxide, 60 ml of N-methylpyrrolidinone and 60 ml of tetrahydrofuran. The mixture is stirred at room temperature for a minimum of 30 minutes and is then cooled to a temperature of 0 to 5° C. The solution obtained from Example 2 is slowly added, with stirring, while maintaining the temperature below 5° C. The reaction mixture is allowed to warm up to room temperature and is stirred at room temperature for 2 hours. The solution is then cooled to a temperature of 0 to 5° C. Thereafter, while stirring and maintaining the temperature below 5° C., 15.5 g of dimethyl sulfate is slowly added. The reaction mixture is then warmed up to room temperature and stirred at room temperature for a minimum of two hours. 60 ml of water is then added with stirring and the reaction mixture is then distilled at reduced pressure (e.g., 50 mm Hg) until the volume has reached approximately 110 ml. 60 ml of water is then added with stirring to the residue and the mixture is then extracted with two 180 ml portions of toluene. The toluene portions are combined and then washed with 15 ml of water. The solution is then dried azeotropically by heating to reflux and the toluene is distilled off until the volume of the residue is approximately 30 ml. Thereafter, 85 ml of anhydrous tetrahydrofuran is added. The tetrahydrofuran solution contains 13.7 g (85% yield) of N-carboethoxynorthebaine having a purity level of greater than 90% as measured by HPLC. The product is an oil and is used in step (d) of the process of the invention (i.e., Example 4) without purification.

EXAMPLE 4

Preparation of Thebaine Bitartrate Monohydrate

Into a 500 ml round-bottomed flask is charged 1.85 g of lithium aluminum hydride and 85 ml of anhydrous tetrahydrofuran. The suspension is vigorously stirred and the tetrahydrofuran solution of N-carboethoxynorthebaine prepared in Example 3 is slowly added. The reaction is exothermic and during the addition, the temperature is maintained below 40° C.

After completion of the addition of the tetrahydrofuran solution of N-carboethoxynorthebaine, the reaction mixture is stirred at room temperature for 4 to 6 hours. Thereafter, 2.3 g of water, 2.3 g of a 15% aqueous solution of sodium hydroxide followed by 5.5 g of water are slowly added. The reaction mixture is then stirred at room temperature for 1 to 2 hours. The solids are filtered off and the filter cake is washed with three 15 ml portions of tetrahydrofuran. The tetrahydrofuran is distilled off under reduced pressure (e.g., 50 mm Hg) and is replaced with methanol, which is added in sufficient quantity to adjust the volume of the reaction mixture to 120 ml.

To the reaction mixture under reflux is added 7.1 g of L-tartaric acid in 10 ml of water. The suspension is cooled and is stirred at 0 to 5° C. for 2 to 3 hours. The solids are filtered off and the filter cake is washed with two 15 ml portions of cold methanol. After drying in vacuo (e.g., 50 mm Hg) at a temperature of 30 to 40° C., 14.5 g (82% yield) of thebaine bitartrate monohydrate is obtained. The purity level of the thebaine bitartrate monohydrate is greater than 99% as measured by HPLC. The total yield of thebaine bitartrate monohydrate based on the starting material, i.e., codeine phosphate hemihydrate, is 61.5%.

What is claimed is:

1. A process for commercially manufacturing thebaine which comprises the steps of:
   (a) converting codeine or a codeine salt into the intermediate N-carboalkoxynorcodeine or N-carboaryloxynorcodeine by reacting the codeine or codeine salt with a chloroformate in the presence of an alkali metal carbonate or alkali metal bicarbonate and an inert solvent at a temperature of about 0 to about 85° C.;
   (b) oxidizing the intermediate N-carboalkoxynorcodeine or N-carboaryloxynorcodeine to yield N-carboalkoxynorcodeinone or N-carboaryloxynorcodeinone using an oxidizing agent in the presence of an inert solvent at a temperature of about 0 to about 60° C.;
   (c) enolizing the intermediate N-carboalkoxynorcodeine or N-carboaryloxynorcodeine with a base in an inert solvent at a temperature of about −20 to about 50° C., and methylating the resultant enolate salt with a methylating agent in an inert solvent at a temperature of about −20 to about 50° C.; and
   (d) reducing the intermediate N-carboalkoxynorthebaine or N-carboaryloxynorthebaine to yield thebaine using a reducing agent in the presence of an inert solvent.

2. The process of claim 1 wherein the alkali metal of the alkali metal carbonate or alkali metal bicarbonate employed in step (a) comprises sodium or potassium.

3. The process of claim 1 wherein the inert solvent employed in step (c) for carrying out the enolization reaction and the subsequent methylation reaction is selected from the group consisting of tetrahydrofuran, N-methylpyrrolidone, dimethylformamide, toluene, dimethyl ether, methyl t-butyl ether and dioxane.

4. The process of claim 2 wherein the alkali metal carbonate comprises potassium carbonate and the chloroformate is selected from the group consisting of methyl, ethyl and phenyl chloroformate.

5. The process of claim 1 wherein the inert solvent employed in step (a) is selected from the group consisting of methylene chloride, chloroform and 1,2-dichloroethane.

6. The process of claim 1 wherein step (b) is carried out by using an oxidizing agent selected from the group consisting of an aluminum alkoxide and a ketone; a potassium alkoxide and a ketone; dimethyl sulfoxide in the presence of oxalyl chloride; manganese dioxide; potassium dichromate in the presence of sulfuric acid; and air in the presence of palladium (II) acetate.

7. The process of claim 6 wherein the oxidizing agent comprises manganese dioxide.

8. The process of claim 1 wherein the base employed in step (c) is selected from the group consisting of sodium hydride, sodium t-butoxide, potassium t-butoxide and lithium diisopropylamide.

9. The process of claim 3 wherein the inert solvent employed in step (c) comprises N-methylpyrrolidone, a mixture of tetrahydrofuran and N-methylpyrrolidone or a mixture of toluene and N-methylpyrrolidone.

10. The process of claim 1 wherein the methylating agent is selected from the group consisting of dimethyl sulfate, dimethyl carbonate, methyl iodide, methyl bromide and diazomethane.

11. The process of claim 1 wherein step (d) is carried out using a reducing agent selected from the group consisting of lithium aluminum hydride, sodium bis(2-methoxyethoxy) aluminum hydride, borane-tetrahydrofuran complex and borane-dimethyl sulfide complex.

12. The process of claim 1 further comprising isolating the thebaine in step (d) in the form of an addition salt.

13. The process of claim 12 wherein the thebaine is isolated in the form of its bitartrate salt by reacting the thebaine with L-tartaric acid in the presence of a solvent selected from the group consisting of a $C_1$–$C_4$ alcohol, acetone and mixtures thereof with water.

14. The process of claim 1 wherein the thebaine in step (d) is manufactured without isolating or purifying any of the intermediates produced in the course of steps (a)–(c).

15. The process of claim 1 wherein the inert solvent employed in step (b) is selected from the group consisting of chloroform, methylene chloride, 1,2-dichloroethane, benzene, toluene, ethyl acetate and tetrahydrofuran.

16. The process of claim 1 wherein the inert solvent employed in step (d) is selected from the group consisting of tetrahydrofuran, dimethyl ether, diethyl ether and methyl t-butyl ether.

* * * * *